United States Patent [19]

Lupo et al.

[11] Patent Number: 5,885,368
[45] Date of Patent: Mar. 23, 1999

[54] PHOTOVOLTAIC CELL

[75] Inventors: Donald Lupo, Frankfurt; Josef Salbeck, Kelkheim, both of Germany

[73] Assignee: Hoechst Aktiengesellschaft, Frankfurt, Germany

[21] Appl. No.: 712,426

[22] Filed: Sep. 11, 1996

[30] Foreign Application Priority Data

Sep. 13, 1995 [DE] Germany ............ 195 33 850.2

[51] Int. Cl.⁶ .................................. H01L 31/0256
[52] U.S. Cl. .................... 136/263; 136/255; 429/111; 257/40; 257/43
[58] Field of Search .................. 136/255, 263; 429/111; 257/40, 43

[56] References Cited

U.S. PATENT DOCUMENTS

| | | | |
|---|---|---|---|
| 4,212,932 | 7/1980 | Calgari et al. | 429/111 |
| 5,026,894 | 6/1991 | Tour et al. | 558/46 |
| 5,536,588 | 7/1996 | Naito | 428/690 |

FOREIGN PATENT DOCUMENTS 0333641  9/1989  European Pat. Off. ........... 429/111

OTHER PUBLICATIONS

Database WPI, Section Ch. Week 9423, Derwent Publications Ltd., London, GB; AN–186208.

Chem. Rev. 1995, vol. 95, pp. 49–68 entitled "Light-Indusced Redox Reactions in nanocrystalline Systems" by Hagfeldt et al.

Chemie in Unserer Zeit pp. 94–95, vol. 2 (1995).

Physik in unserer Zeit, 1990, vol. 6, p. 237 ff.

*Primary Examiner*—Nam Nguyen
*Attorney, Agent, or Firm*—Frommer Lawrence & Haug LLP

[57] ABSTRACT

A photovoltaic cell having a charge transport layer comprising a hole conductor material is disclosed and claimed. The photovoltaic cell comprising a light absorbing layer having a semiconductor material with a bassed gap of at least 3.0 Ev, the surface of the semiconductor having a roughness of >20, optionally a sensitizer layer, a charge transport layer comprising one or more spiro compounds of the formula (I) as a hole conductor material

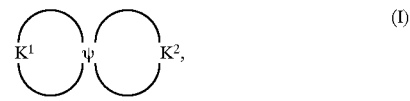

where

Ψ is C, Si, Ge or Sn, and $K^1$ and $K^2$, independently of one another, are conjugated systems, and a counter electrode.

14 Claims, 4 Drawing Sheets

Fig. 1

Fig. 3: Photovoltaic current in short-circuited cell
Intensity about 750 W/m²

Fig. 4: Photovoltaic characterization

PHOTOVOLTAIC CELL

RELATED APPLICATION

This application claims priority to German Application No. 195 33 850.2 filed Sep. 13, 1995, incorporated herein by reference.

BACKGROUND OF THE INVENTION

Owing to the rising world demand for electrical energy and the limited reserves of coal, oil and gas, which in addition liberate the greenhouse gas $CO_2$ on combustion, the generation of electric power from sunlight has been the subject of increased interest in recent years.

FIELD OF THE INVENTION

A photovoltaic cell is a component in which light is converted directly into electrical energy. Beside two electrodes it comprises at least a light absorbing layer and a charge transport layer. If the light is sunlight, one speaks of a solar cell.

Although the photovoltaic effect, i.e. the generation of an electric potential across a pn junction on irradiation with light, was observed by Becquerel as early as 1893, the first functional solar cells were only able to be produced with the development of semiconductor technology in the 1940s and 1950s.

The solar cells used nowadays in most cases contain as light-absorbing layer a semiconductor material, usually silicon, but for this application the silicon has to meet very high demands in respect of purity and quality of processing. As a result, solar cells are nowadays not competitive for many applications for cost reasons.

In contrast, a dye-sensitized solar cell as was developed in the 1960s by H. Tributsch uses a material having a very large band gap, e.g. titanium dioxide, as a semiconductor. Such a semiconductor absorbs little sunlight, for which a dye (chromophore) is applied to the semiconductor.

If a dye molecule absorbs a photon, this causes excitation of an electron into the lowest unoccupied molecular orbital. From this, it can then be injected into the conduction band of the semiconductor. The semiconductor thus serves predominantly for the transport of electrons. For this purpose, no particular purity and perfection of the material is necessary. It can, for example, simply be painted from a powder suspension onto conductive glass.

DESCRIPTION OF THE PRIOR ART

EP-A 0 333 641 describes a photoelectrochemical cell which comprises a nanoporous metal oxide semiconductor, i.e. a semiconductor having an extremely roughened and thus enlarged surface. In this cell, the charge transport between semiconductor/chromophore layer and counter electrode occurs through an electrolyte solution. Although good results are obtained using such cells, the property profile of such a device is still clearly capable of improvement. A particular disadvantage is that the electron has to be returned to the dye by means of diffusion of ions. As a result, the only suitable redox systems are those which are small enough to penetrate into the pores of the nanocrystalline semiconductor layer. Even in the case of the best redox system up to now, viz. $I_2/I_3^-$, about 40% of the theoretically available energy is lost as heat and the efficiency of the energy conversion is limited to about 10% in sunlight. In addition, a compromise between viscosity and mobility of the ions always has to be found for the electrolyte, and this does not ideally meet either requirement.

SUMMARY OF THE INVENTION

It has now surprisingly been found that the above described disadvantages can be at least reduced if the electrolyte layer in the cell discussed above is replaced by a charge transport layer comprising a hole conductor material.

The invention accordingly provides a photovoltaic cell having a charge transport layer comprising a hole conductor material.

As a result of the use of the hole conductor material in place of the electrolyte, the charge transport is no longer limited by the diffusion of the ions. In addition, the relevant energy levels of the layer can be matched in such a way that the efficiency for sunlight conversion can be improved to $\geq 18\%$.

DETAILED DESCRIPTION OF THE INVENTION

On a conductive support 11 (FIG. 1), which can serve as electrode/contact and, for example, consists of a metal or indium-tin oxide (ITO), there is applied as a light absorbing layer a semiconductor 12 which preferably has a surface having a roughness factor >1. The cell of the invention preferably has a chromophore, here shown as chromophore layer 13, on the surface of the semiconductor. In the context of the invention the term "light absorbing layer" encompasses a semiconductor layer as well as a combination semiconductor/chromophore even though the actual absorption in this case takes place almost exclusively in the chromophore. This is adjoined by the charge transport layer 14 which, according to the invention, comprises a hole conductor material. It is bounded on one side by the counter electrode 15 which can, for example, consist of a conductive glass, plastic having a conductive coating, metal or another conductive, preferably translucent, material. The cell 1 is preferably closed off top and bottom by insulating layers 16 and 17. It can have a lateral enclosure not shown in the figure, for example a frame comprising an electrically insulating material such as plastic or glass. However, the use of a hole conductor material in place of the liquid electrolyte makes such a lateral frame not necessary in principle. At least one side of the cell has to allow the light to be converted into electrical energy to pass through so that it can reach the chromophore or the semiconductor. The cell of the invention additionally has devices for outputting the electric current generated by the cell (not shown in the figure).

For the purposes of the invention, a hole conductor material is a material which can conduct a positive charge resulting from the absence of an electron, thus decoupling mass transport and charge transport.

Generally suitable are electron-rich, preferably organic compounds which are oxidizable, preferably reversibly. It is generally assumed that charge transport in an organic hole conductor material occurs via the formation of free-radical cations.

The oxidation potential can here be varied over a wide range and can be matched to the specific energy levels of the semiconductor or sensitizer. It is preferably between the energy of the ground state and 700 mV, preferably 400 mV, particularly preferably 300 mV, above the ground state.

Preference is given to using hole conductor materials in which no mass transport takes place, viz. in which charge and mass transport are fully decoupled.

Furthermore, preference is given to solid, in particular, amorphous hole conductor materials.

For the purposes of the invention it is preferred that the hole conductor layer of the invention is applied in an amorphous state in the photovoltaic cell of the invention.

The term amorphous is used to describe the state of solids whose molecular building blocks are arranged not in crystal lattices but irregularly. Unlike a crystal in which the atoms have both short-range order (i.e. constant distances to nearest neighbors) and long-range order (regular repetition of a unit cell), the amorphous state has only short-range order. The amorphous material has no physically distinguishable direction; it is isotropic. All amorphous materials are, to varying degrees, energetically unstable relative to the lower-energy crystalline state. In the diffraction of X-rays, electrons and neutrons, amorphous solids do not give sharp interference rings, as in a crystal, but only diffuse interference rings at low diffraction angles (halos).

The amorphous state is thus clearly distinguishable from the crystalline, liquid, or liquid-crystal state.

Particular preference is given to hole conductor materials which are soluble in organic solvents, and also hole conductor materials which are fusible. Examples of organic solvents, to which the invention is nevertheless not restricted, are chloroform, benzene, chlorobenzene, cyclohexanone, toluene, tetrahydrofuran, anisol, cresol, xylene, methyl lactate, methylene chloride, hexane and other aliphatic, aromatic or alcoholic solvents. For producing a hole conductor layer according to the invention, it is sufficient for the hole conductor material to be soluble in an organic solvent or to be fusible. For the purposes of the invention, soluble means a solubility of at least 1.0 g/l at 25° C. in an organic or inorganic solvent, preferably in one of the abovementioned solvents.

Furthermore, particular preference is given to hole conductor materials which owing to their size can diffuse into the pores of a rough semiconductor layer.

In addition, it is preferred that the molecules of the hole transport layer have a molecular size comparable to that of the molecules of any sensitizer used, so that the hole conductor molecules can come into close contact with the sensitizer molecules located in the pores of the semiconductor surface. Particularly preferably, the hole conductor molecules are larger than corresponding sensitizer molecules by a factor of less than 20, very particularly preferably less than 10. Very particular preference is given to hole conductor materials in which the voltage loss across the hole conductor layer on irradiation with sunlight is <500 mV, preferably <50 mV, particularly preferably <20 mV. The hole conductor layer generally has a thickness of from 0.1 to 20 $\mu$m, preferably from 1 to 15 $\mu$m. The charge carrier mobility of the hole conductor material is preferably at least $10^{-5}$ cm$^2$/Vs, in particular from $10^{-3}$ to 10 cm$^2$/Vs.

Very particularly preferred hole conductor materials are spiro and heterospiro compounds of the formula (I), (I)

where

Ψ is C, Si, Ge or Sn, preferably C, Si or Ge, particularly preferably C or Si and in particular C and $K^1$ and $K^2$ are, independently of one another, conjugated systems.

Spiro compounds are compounds in which two ring systems are linked by a single, tetravalent atom. This atom is designated as the spiroatom, as is explained in Handbook of Chemistry and Physics 62$^{nd}$ edition (1981–2), CRC Press, pages C-23 to C-25. For the purposes of the invention, the term spiro compound refers to monomeric and polymeric carbospiro and heterospiro compounds.

Preferred compounds of the formula (I) are 9,9'-spirobifluorene derivatives of the formula (II), (II)

where Ψ is as defined above and the benzo groups can be, independently of one another, substituted and/or fused.

Particular preference is given to spirobifluorene derivatives of the formula (III), (III)

where the symbols and indices have the following meanings:

Ψ is C, Si, Ge or Sn, preferably C, Si, Ge, particularly preferably C, Si, in particular C, K, L, M, N are identical or different and are each a group of the formulae -continued R are identical or different and are as defined for K, L, M, N or are hydrogen, a linear or branched alkyl, alkoxy or carboalkoxy group having from 1 to 22, preferably from 1 to 15, particularly preferably from 1 to 12, carbon atoms, —CN, —NO$_2$, —NR$^1$R$^2$, —Ar or —O—Ar;

Ar is phenyl, biphenyl, 1-naphthyl, 2-naphthyl, 2-thienyl, 2furanyl, where each of these groups can bear one or two radicals R;

m, n, p are 0, 1, 2 or 3;

X, Y are =CR— or =N—;

Z is —O—, —S—, —NR—, —CRR—, —CH=CH—, —CH=N—;

R$^1$ and R$^2$ are hydrogen, a linear or branched alkyl group having from 1 to 22 carbon atoms, —Ar or 3-methylphenyl.

Preferred compounds of the formula (III) are those of the formulae (IIIa)–(IIIg)

IIIa) K=L=M=N and is a group of the formulae:

-continued

R = C$_1$–C$_{22}$-alkyl, C$_2$H$_4$SO$_3^-$

IIIb) K=M=H and N=L and is a group of the formulae:

-continued

IIId) K=M and is a group of the formulae:

and N = L and is a group of the formulae:

R = $C_1$–$C_{22}$-alkyl, $C_2H_4SO_3^-$

IIIe) K=L=H and M=N and is a group of the formulae:

IIIf) K=L and is a group of the formulae:

R = $C_1$–$C_2$-alkyl, $C_2H_4SO_3^-$ and N = L and is a group of the formulae:

-continued

IIIg) K=L and is a group of the formulae:

and M = N and is a group of the formulae:

R = $C_1$–$C_{22}$-alkyl, $C_2H_4SO_3^-$

Particularly preferred compounds of the formula (III) are those of the formulae (IIIaa) to (IIIdb):

(IIIaa) K=L=M=N and is a group of the formulae:

(IIIba) K=M=H and N=L and is a group of the formulae:

(IIIca) K=M and is a group of the formulae:

and N=L and is:

(IIIda) K=M and is a group of the formulae:

and N=L and is:

(IIIab) K=L=M=N and is a group of the formulae:

(IIIbb) K=L H and M=N and is a group of the formulae:

(IIIcb) K=L and is a group of the formulae:

and M=N and is:

(IIIdb) K=L and is a group of the formulae:

and M=N and is:

Very particularly preferred spiro compounds are those of the formula (IV),

(IV)

where the symbols have the following meanings:

Ψ is C or Si, preferably C;

K, L, M and N are identical or different and are each one of the groups G1 to G14:

G7

G8

G9

G10

G11 and $R^5$, $R^6$ can also be identical or different and be hydrogen or a linear or branched alkyl, alkoxy or ester group having from 1 to 22 carbon atoms, —CN or —NO$_2$.

Most preferred spiro compounds of the formula (IV) are 2,2',4,4',7,7'-hexakis(biphenylyl)-9,9'-spirobifluorene, 2,2',4,4',7,7'-hexakis(terphenylyl)-9,9'-spirobifluorene, 2,2',4,4'-hexakis(biphenylyl)-9,9'-spirobi-9-silafluorene and 2,2',4,4',7,7'-hexakis(terphenylyl)-9,9'-spirobi-9-silafluorene.

The spiro and heterospiro compounds used according to the invention are prepared by methods known per se, as are described in EP-A 0 676 461 and standard works on organic synthesis, e.g. Houben-Weyl, Methoden der Organischen Chemie, Georg-Thieme-Verlag, Stuttgart and in the appropriate volumes of the series "The Chemistry of Heterocyclic Compounds" by A. Weissberger and E. C. Taylor (editors).

The preparation is carried out under reaction conditions which are known and suitable for said reactions. Use can here also be made of variants which are known per se and are not mentioned in more detail here.

a) Carbospiro compounds

Compounds of the formula (III) are obtained, for example, starting from 9,9'-spirobifluorene whose synthesis is described, for example, by R. G. Clarkson, M. Gomberg, J. Am. Chem. Soc. 1030, 52, 1930.

EXAMPLES

Compounds of the formula (IIIa) can be prepared, for example, starting with a tetrahalogenation in the 2, 2', 7 and 7' positions of 9,9'-spirobifluorene and subsequent substitution reaction (see, for example, U.S. Pat. No. 5,026,894) or via a tetraacetylation of the 2, 2', 7 and 7' positions of 9,9'-spirobifluorene with subsequent C—C linkage after conversion of the acetyl groups into aldehyde groups or building up a heterocycle by conversion of the acetyl groups into carboxyl groups. Compounds of the formula (IIIb) can be prepared, for example, by a similar method to those of the formula IIIa, with the stoichiometric ratios in the reaction being selected such that the positions 2,2' or 7,7' are functionalized (see, for example, J. H. Weisburger, E. K. Weisburger, F. E. Ray, J. Am. Chem. Soc. 1959, 72,4253; F. K. Sutcliffe, H. M. Shahidi, D. Paterson, J. Soc. Dyers Colour 1978, 94, 306 and G. Haas, V. Prelog, Helv. Chim. Acta 1969, 52 1202).

Compounds of the formula (IIIc) can be prepared, for example, via a dibromination in the 2 and 2' positions and subsequent diacetylation in the 7 and 7' positions of 9,9'-spirobifluorene and subsequent reaction by a similar method to the compounds (IIIa).

Compounds of the formulae (IIIe)–(IIIg) can be prepared, for example, by selection of suitably substituted starting compounds in building up the spirobifluorene, e.g. 2,7-dibromospirobifluorene can be obtained from 2,7-dibromofluorenone and 2,7-dicarbethoxy-9,9'-spirobifluorene can be produced using 2,7-dicarbethoxyfluorenone. The free 2' and 7' positions of the spirobifluorene can then be further substituted independently.

For the synthesis of the groups K, L, M, N, reference may be made, for example, to DE-A 23 44 732, 24 50 088, 24 29 093, 25 02 904, 26 36 684, 27 01 591 and 27 52 975 for compounds having 1,4-phenylene groups; DE-A 26 41 724 for compounds having pyrimidin-2,5-diyl groups; DE-A 40 26 223 and EP-A 03 91 203 for compounds having pyridin-2,5-diyl groups; DE-A 32 31 462 for compounds having pyridazin-3,6-diyl groups; N. Miyaura, T. Yanagi and A. Suzuki in Synthetic Communications 1981, 11, 513 to 519, DE-A-39 30 663; M. J. Sharp, W. Cheng, V. Snieckus, Tetrahedron Letters 1987, 28, 5093; G. W. Gray, J. Chem. Soc. Perkin Trans II 1989, 2041 and Mol. Cryst. Liq. Cryst. 1989, 172, 165; Mol. Cryst. Liq. Cryst. 1991, 204, 43 and 91; EP-A 0 449 015; WO 89/12039; WO 89/03821; EP-A 0 354 434 for the direct linking of aromatics and heteroaromatics.

The preparation of disubstituted pyridines, disubstituted pyrazines, disubstituted pyrimidines and disubstituted pyridazines is described, for example, in the appropriate volumes of the series "The Chemistry of Heterocyclic Compounds" by A. Weissberger and E. C. Taylor (editors).

b) Heterospiro compounds

Such compounds of the formula (III) are obtained, for example, starting from bis[biphenyl-2,2'-diyl]silane (=9,9'-spirobi(9H-)-silafluorene) (V) whose synthesis is described, for example, by H. Gilman, R. D. Gorsich, J. Am. Chem. Soc. 1958, 80, 3243.

(V)

Heterospiro compounds of the formula (IIIa) can be prepared, for example, starting with a tetrahalogenation in the 2, 2', 7 and 7' positions of 9,9'-spirobi-9-silafluorene and a subsequent substitution reaction which is known from analogous C-spiro compounds (see, for example, U.S. Pat. No. 5,026,894) or via a tetraacetylation of the 2, 2', 7 and 7' positions of 9,9'-spirobi-9-silafluorene with subsequent C—C linkage after conversion of the acetyl groups into aldehyde groups or build up of a heterocycle by conversion of the acetyl groups into carboxyl groups.

Compounds of the formula (IIIb) can be prepared, for example, using a similar method to those of the formula (IIIa), with the stoichiometric ratios in the reaction being selected such that the positions 2,2' or 7,7' are functionalized (see, for example, J. H. Weisburger, E. K. Weisburger, F. E. Ray, J. Am. Chem. Soc. 1959, 72, 4253; F. K. Sutcliffe, H. M. Shahidi, D. Paterson, J. Soc. Dyers Colour 1978, 94, 306 and G. Haas, V. Prelog, Helv. Chim. Acta 1969, 52, 1202).

Compounds of the formula (IIIc) can be prepared, for example, via a dibromination in the 2 and 2' positions with subsequent diacetylation in the 7 and 7' positions of 9,9'-spirobi-9-silafluorene and subsequent reaction using a method similar to that for the compounds (IIIa).

Compounds of the formulae (IIIe)–(IIIg) can be prepared, for example, by selection of suitably substituted starting compounds in building up the spirosilabifluorene according to the two reaction schemes below:

It is also possible to use other synthetic sequences with which those skilled in the art are familiar, for example nitration, reduction, diazotization and the Sandmeyer reaction. For the synthesis of the groups K, L, M, Q, reference is made to the corresponding carbospiro compounds.

It is also possible in principle to use oligomers or polymers comprising the corresponding spiro units, as long as the compounds are able to penetrate into the pores of the nanocrystalline semiconductor. Such compounds are described in EP-A 0 707 020; WO-A 96/17 036; DE-A 196 06 511; DE-A 196 14 971 and DE-A 196 15 128; these documents are hereby expressly incorporated by reference, their disclosure is by citation part of the present application.

The photovoltaic cell according to the invention comprises as a light absorbing layer preferably a semiconductor, which preferably has a very large band gap, more preferably at least 3.0 eV, particularly preferably above 3.0 eV.

Suitable semiconductors are thus preferably metal oxide semiconductors, in particular the oxides of the transition metals and also the elements of the third main group and the fourth, fifth and sixth transition groups (of the Periodic Table of the Elements), viz. titanium, zirconium, hafnium, strontium, zinc, indium, yttrium, lanthanum, vanadium, niobium, tantalum, chromium, molybdenum, tungsten, but also oxides of zinc, iron, nickel or silver, perovskites such as $SrTiO_3$, $CaTiO_3$ or oxides of other metals of the second and third main group or mixed oxides or oxide mixtures of these metals. However, it is also possible to use any other metal oxide having semiconductor properties and a large energy difference (band gap) between the valence band and conduction band.

The particularly preferred semiconductor material is titanium dioxide.

The semiconductor preferably has a roughness factor of greater than 1, particularly preferably greater than 20, very particularly preferably greater than 150.

The roughness factor is defined as the ratio of an actual/effective surface area to the projected area of this surface of a body, in this case the surface of the semiconductor.

The roughness factor can be determined, for example, by gravimetric adsorption methods as are described, for example, in F. Kohlrausch, Praktische Physik, Volume 1, p. 397 (Stuttgart: B. G. Teubner, 1985). In general, the size of the pores is 5–200 nm, preferably 10–50 nm.

A process for producing polycrystalline metal oxide semiconductor layers using the sol-gel process (described in detail in, for example, Stalder and Augustynski, J. Electrochem. Soc. 1979, 126, 2007), where during the process step comprising the hydrolysis of the metal alkoxide the relative humidity of the surrounding atmosphere can be in a range from 30% to 80% and is kept constant to within ±5%, preferably ±1%, gives metal oxide semiconductor layers by means of which a particularly high electric yield can be achieved in photovoltaic cells of the invention.

The rough surface having a polycrystalline structure offers an area increased by the roughness factor for a, preferably monomolecular, surface layer of the chromophore. As a result, light incident on an area having a particular size is converted into electrical energy with a significantly higher yield. The semiconductor can be regarded as transparent for the incident light. However, light is partially reflected on the surface and some of it reaches adjacent surfaces. The light which penetrates into the semiconductor and is not absorbed or converted impinges, partly directly and partly indirectly and a further part of it indirectly after total reflection at the surface on the exit side, on chromophore molecules, thus achieving a significantly higher light yield.

As an example for the production of a titanium oxide layer ($TiO_2$) having a high roughness factor on a titanium substrate, the sol-gel process is described below.

The titanium substrate made of pure titanium having a purity of about 99.5% is first cleaned for about 30 minutes in boiling HCl having a concentration of about 18%. The titanium ethoxide solution can be obtained, for example, by dissolving 21 mmol of $TiCl_4$ in 10 ml of very pure ethanol (puriss.). This solution is then diluted with very pure methanol (puriss.) in order to obtain a titanium concentration in the range from about 25 to 50 mg/ml. One drop of the solution is placed on the titanium substrate and the titanium alkoxide is hydrolyzed at room temperature over a period of about 30 minutes at a humidity of 48±1%. The substrate together with the hydrolyzed layer is then heated at about 450° C. for about 15 minutes. This process is repeated a number of times. After repeating it 10–15 times, the $TiO_2$ layer has reached a thickness of about 20 µm. The substrate together with the layer is then baked out at about 500° C. for about 30 minutes in a pure argon atmosphere (e.g. 99.997%). The $TiO_2$ layer thus produced has a roughness factor in the region of 200. Such metal oxide semiconductor layers (other metals are also possible) can be produced on other substrates using similar methods. The upper layers of the semiconductor can, if desired, be doped with a divalent or trivalent metal as described, for example, in WO-A 91/16719.

The sensitivity, i.e. the photoelectronic yield for visible light, thus for sunlight too, can be increased by chromophores, also known as sensitizers or dyes, to be chemically bound (chemisorbed) as charge carriers on or in the surface of the semiconductor. The two functions of light absorption and charge carrier separation are separated in these photoelectronic systems. The light absorption is taken over by the chromophore in the surface region and the separation of the charge carriers occurs at the semiconductor/chromophore boundary. Various chromophores have different spectral sensitivities. The selection of the chromophore can thus be matched to the spectral composition of the light of the light source in order to increase the yield as much as possible. Suitable chromophores, i.e. sensitizers, are, in particular, the transition metal complexes of the type metal($L_3$), metal($L_2$) where the metal is ruthenium or osmium (e.g. ruthenium tris(2,2'-bipyridyl-4,4'-dicarboxylates), ruthenium cis-(diaqua) bipyridyl complexes such as ruthenium cis-(diaqua)bis(2,2'-bipyridyl-4,4'-dicarboxylates)) and also porphyrins (e.g. zinc tetra(4-carboxyphenyl)porphyrin) and cyanides (e.g. iron hexacyanide complexes) and phthalocyanines. The chromophores can be chemisorbed, adsorbed or otherwise firmly attached in the region of the surface of the metal oxide semiconductor. Favorable results are obtained, for example, using chromophores which are bound by means of carboxylic acid or phosphonic acid ligands to the surface of the metal oxide semiconductor.

Suitable chromophores are also described, for example, in Chem. Rev. 1995, 49–68.

Particular preference is given to the chromophores (VIII) and (IX), whose synthesis and properties are described in J. Chem. Soc. Chem. Comm. 1995, 65.

The chromophore, for example $RuL_3^{4-}$, is applied, for example, by dipping the substrate having the oxide layer into an ethanolic solution of $2\times10^{-4}M$ $RuL_3^{4-}$ for about an hour. Other chromophores can be applied to titanium oxide or other metal oxide semiconductors using similar methods.

Figure 1:
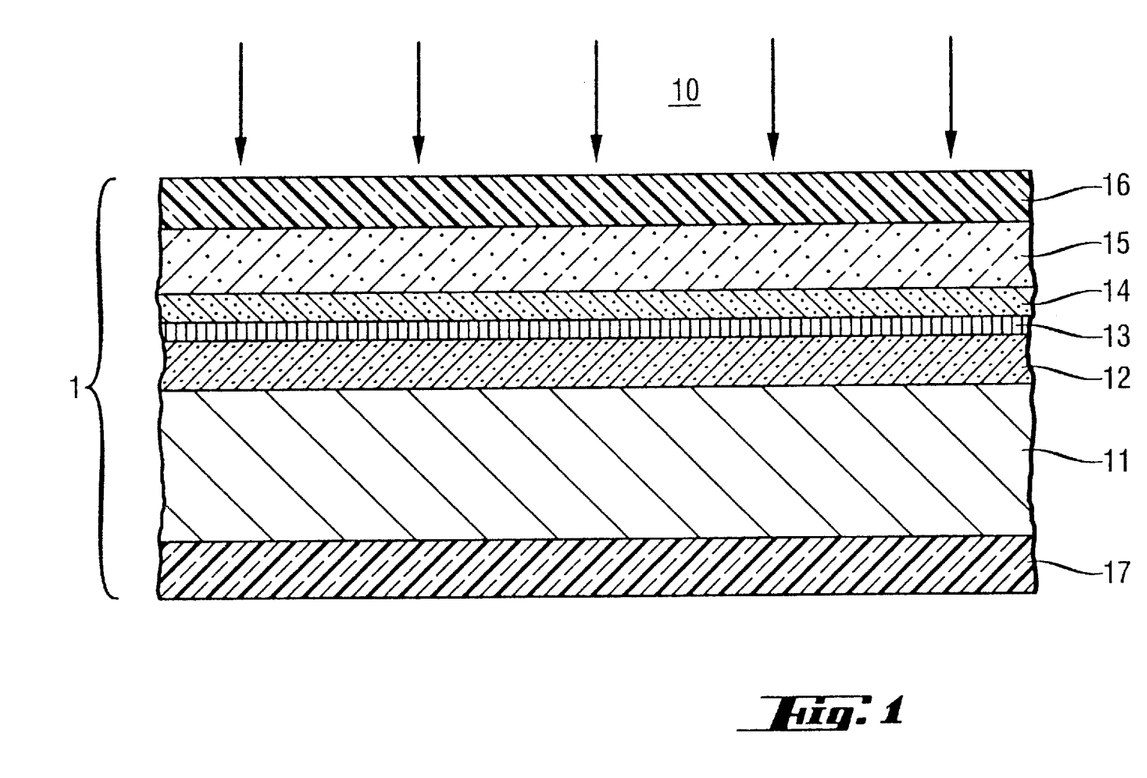
FIG. 1 shows a preferred embodiment of the cell 1 of the invention (not to scale).

Suitable materials for the electrode 15 are stable, metallic conductors, e.g. Au, Ag, Pt, Cu or other metals. However, for some applications it is also possible to use preferably translucent conductive substances such as doped metal oxides, e.g. indium tin oxide, Sb-doped tin oxide or Al-doped zinc oxide. The work function of the electrode material used is here preferably matched to the ionization potential of the hole transport material used.

The electrode can, as described in EP-A 0 333 641, be applied to a transparent substrate, e.g. glass, and be joined to the hole transport layer. In the cell described in the present invention, it is preferably applied by physical deposition methods, e.g. vapor deposition or sputtering, directly onto the hole transport layer, without a second glass plate being necessary. This process is preferable in applications where the weight of the cell is to be reduced.

If desired, the electrode can also be coated with a further semiconductor, as described in WO-A 93/19479.

Suitable electrically insulating materials 16 and 17 and materials for any lateral frame for the cell of the invention are, for example, plastic or glass.

Therefore, in a further aspect of the invention there is provided a process for producing a photovoltaic cell, which comprises a) applying a semiconductor colloid to a conductive solid support, b) optionally applying a dye to the semiconductor, c) applying a transport layer comprising a hole conductor material to the dye, d) applying the counter electrode to the transport layer and e) applying an insulating layer to the counter electrode.

If desired, the cell can also be sealed, for example using an adhesive or a film.

The photovoltaic cell of the invention generally has a thickness of from 5 to 20 mm (including substrate).

To avoid reflection losses, it can be provided with an antireflection coating having one, two, or more layers.

To increase the light yield, the reverse side of the cell can be constructed in such a way that light is reflected diffusely back into the cell.

A further increase in the light yield can be achieved, for example, by the incident sunlight being concentrated, for example, by mirrors or Fresnel lenses.

The cell of the invention can also be part of a tandem cell; in such devices a plurality of subcells convert light from different spectral regions into electrical energy.

The cell of the invention is used as a photocell, i.e. it serves to generate electrical energy from light. It is preferably a solar cell, i.e. a device for generating electrical energy from sunlight.

The contents of the german patent application 195 33 850.2, whose priority is claimed by the present application, is hereby expressly incorporated by reference; it is, as is also the abstract of the present application, by citation a part of the description:

The invention is illustrated by the examples.

SYNTHESIS EXAMPLES

Example 1

9,9'-Spirobifluorene 7.66 g of magnesium turnings and 50 mg of anthracene were placed under argon in 100 ml of dry diethyl ether in a 1 l three-necked flask fitted with reflux condenser and reacted with 75 g of 2-bromobiphenyl dissolved in 60 ml of dry diethyl ether. 56.77 g of 9-fluorenone dissolved in 500 ml of dry diethyl ether were then added dropwise while stirring. After addition was complete, boiling was continued for 2 hours. The precipitated yellow magnesium complex was filtered off with suction and washed with ether. The yellow magnesium complex filtered off was then hydrolyzed in a solution of 48 g of ammonium chloride in 800 ml of ice water. After stirring for 60 minutes, the fluorenol formed was filtered off with suction, washed with water and sucked dry. The dried product was then boiled under reflux for 2 hours in about 800 ml of glacial acetic acid with addition of 3 ml of concentrated HCl. After cooling, the product was filtered off with suction, washed with water and dried. To purify it further, it was recrystallized once from acetone. This gave 86 g of 9,9'-spirobifluorene as colorless crystals (82% yield).

Example 2

Synthesis of 2,2'4,4'7,7'-hexabromo-9,9'-spirobifluorene 200 mg of anhydrous $FeCl_3$ were added to a solution of 3.16 g (10 mmol) of 9,9'-spirobifluorene in 20 ml of methylene chloride and the mixture was treated with ultrasound. The reaction flask was protected from light using aluminium foil. Subsequently, 9.85 g (3.15 ml, 62 mmol) of bromine in 5 ml of methylene chloride were added dropwise at the boiling point over a period of 15 minutes. The solution was boiled under reflux and treated with ultrasound for a further 20 hours. After cooling, petroleum ether was added and the mixture was filtered with suction. The product was further purified by recrystallization from THF/methanol and was dried for 5 hours at 80° C. Yield: 6.15 g (77%) of colorless crystals.

Example 3

Synthesis of 2,2'4,4'7,7'-hexabiphenylyl-9,9'-spirobifluorene (Compound 1)

In a 250 ml two-necked flask fitted with reflux condenser and precision glass stirrer, 1.6 g of hexabromospirobifluorene and 3 g of biphenylboronic acid were slurried in a mixture of 50 ml of toluene and 50 ml of 1M potassium carbonate solution. The mixture was heated to reflux under nitrogen and 115 mg of tetrakis(triphenylphosphine) palladium in 5 ml of toluene were added. Subsequently, the mixture was boiled under reflux for a further 7 hours while stirring. After the reaction was complete, the cooled solution was filtered and the filtrate was shaken twice with water (chloroform was added to improve phase separation). The organic phase was dried over sodium sulfate, filtered through a short silica gel column and the solvent was subsequently taken off on a rotary evaporator. The product was further purified by recrystallization from dichloromethane/ pentane. This gave 2 g(80%) of colorless crystals which displayed a blue fluorescence under UV light.

Example 4

2,2'7,7'-Tetraiodo-9,9'-spirobifluorene

In a 100 ml two-necked flask fitted with reflux condenser and drying tube, 3.16 g (10 mmol) of 9,9'-spirobifluorene dissolved in 30 ml of chloroform were admixed at room temperature with 5.8 g (22.8 mmol) of iodine. 10.75 g (25 mmol) of bis(trifluoroacetoxy)iodobenzene were subsequently added. The reaction mixture warmed to about 40° C. with formation of a pale precipitate. After 1.5 hours, the precipitated product was filtered off with suction, washed with chloroform and dried. The chloroform solutions are combined and washed in succession with saturated sodium sulfite solution, saturated sodium carbonate solution and water. After drying over sodium sulfate, the solution was evaporated and a second product fraction was obtained. Both product fractions were combined, boiled in acetone and, after cooling, filtered off with suction. This gave 2,2',7,7'-tetraiodo-9,9'-spirobifluorene as a finely crystalline colorless powder in virtually quantitative yield (8.1 g).

$^1$H-NMR ($CDCl_3$, ppm): 6.98 (d, J=1.48 Hz, 4 H, H-1, 1',8,8'); 7.54 (dd, J=7.88, 1.48 Hz, 4 H, H-3,3',6,6'); 7.72 (d, J=7.88 Hz, 4 H, H4,4',5,5').

Example 5

2,2'7,7'-Tetrakis(diphenylamino)-9,9'-spirobifluorene (Compound 2)

2.1 g (2.56 mmol) of tetraiodospirobifluorene were heated to boiling for 48 hours under nitrogen with 2.25 g (13.3 mmol) of diphenylamine with addition of 2.76 g (20 mmol) of potassium carbonate, 635 mg (10 mmol) of copper powder and 208 mg (0.79 mmol) of 18-crown-6 in 10 ml of o-dichlorobenzene. After cooling, the inorganic constituents were filtered off and washed with warm dichlorobenzene. The dichlorobenzene was removed by vacuum distillation (100 mbar, 135°–140° C.). The residue was dissolved in chloroform, filtered through a short silica gel column and evaporated. The product was purified by recrystallization first from chloroform/acetone and subsequently from chloroform/diethyl ether with addition of 2 drops of hydrazine hydrate. This gave 1.4 g (56% yield) of 2,2',7,7'-tetrakis (diphenylamino)-9,9'-spirobifluorene in the form of very fine, yellowish-white crystalline needles.

$^1$H-NMR (CDCl$_3$, ppm): 6.69 (d, J=1.83 Hz, 4 H, H-1, 1',8,8'); 6.92 (dd, J=8.18, 1.99 Hz, 4 H, H-3,3',6,6'); 6.98 (m, 24 H); 7.20 (m, 16 H); 7.45 (d, J=8.18 Hz, 4 H, H-4,4',5,5').

Example 6

N, N, N', N', N", N", N'", N'"-Octakis(4-methoxyphenyl)-9,9'-spirobifluorene-2,2',7,7'-tetramine The reaction of tetraiodospirobifluorene with 4,4'-dimethoxydiphenylamine using a method similar to the above procedure gave a comparable yield of N, N, N', N',N", N", N'", N'"-octakis(4-methoxyphenyl)-9,9'-spirobifluorene-2,2',7,7'-tetramine as a yellowish crystalline powder.

$^1$H-NMR (CDCl$_3$, ppm): 3.76 (s, 24 H, OCH$_3$); 6.54 (d, J=1.99 Hz, 4 H, H-1,1',8,8'); 6.75 (dm, J=9.07 Hz, 16 H); 6.79 (dd, J=8.18, 1.99 Hz, 4 H, H-3,3',6,6'); 6.90 (dm, J=9.07 Hz, 16 H); 7.35 (d, J=8.18 Hz, 4 H, H-4,4',5,5')

Use examples

Example 7

The Compound 1 described in Example 3 was dissolved in a concentration of 50 g/l in tetrahydrofuran. A substrate comprising conductive, SnO$_2$-coated glass on one side of which a smooth layer of Nb-doped titanium dioxide had been applied (Substrate I) was coated by dipping into the above solution. Both sides of the substrate were coated in one dipping procedure. A thin layer of gold was subsequently deposited by thermal vapor deposition on the side coated with titanium dioxide. The side coated with titanium dioxide and gold is described hereinafter as the active side, the other is described as the inactive side.

The specimen thus prepared was mounted in an optical apparatus comprising a high-pressure lamp, optical filters, lenses and mountings. The use of filters and moving of the lenses enabled the intensity to be varied. In addition, the light having a wavelength of less than 380 nm was essentially filtered out in order to prevent direct excitation of Compound 1 by light. The specimen was mounted with the inactive side facing the lamp, so that residual light in the range of the absorption spectrum of Compound 1 was absorbed by the layer located on the inactive side. As a result of the doping with Nb, the titanium dioxide layer had a low absorption between 400 and 450 nm, so that it was excited by the lamp.

Contacts were applied to the gold and SnO$_2$ layers and a current measuring instrument was connected while the specimen was illuminated. No external voltage was applied. During illumination of the specimen, a current was observed and this disappeared again after shutting off the light source. Comparison with a thermal treatment of the specimen showed that the current observed was a genuine photovoltaic current which arises as a result of injection of positive charge carriers (holes) into the layer of Compound 1 and transport of the holes through this layer. The intensity of the illumination was varied over a factor of ten; over this range, the photovoltaic current increased linearly with the intensity.

Example 8

Compound 1 was dissolved at a concentration of 50 g/l in tetrahydrofuran. A substrate comprising a conductive, SnO$_2$-coated glass on one side of which there had been applied a nanoporous layer of titanium dioxide containing about 30% of the rutile phase, which still has weak absorption above 400 nm, and having a surface with a roughness factor of 700–1000 (Substrate II) was coated by dipping into the above solution. Both sides of the substrate were coated in one dipping procedure. A thin layer of gold was subsequently applied by thermal vapor deposition to the side coated with titanium dioxide. The side coated with titanium dioxide and gold is hereinafter referred to as the active side, the other is referred to as the inactive side.

The specimen thus prepared was mounted in the optical apparatus described in Example 7. The specimen was mounted with the inactive side facing the lamp, so that residual light in the range of the absorption spectrum of Compound 1 was absorbed by the layer located on the inactive side. Owing to the presence of the rutile phase, the titanium dioxide layer had a small absorption between 400 and 430 nm, so that this was excited by the lamp.

Figure 2:
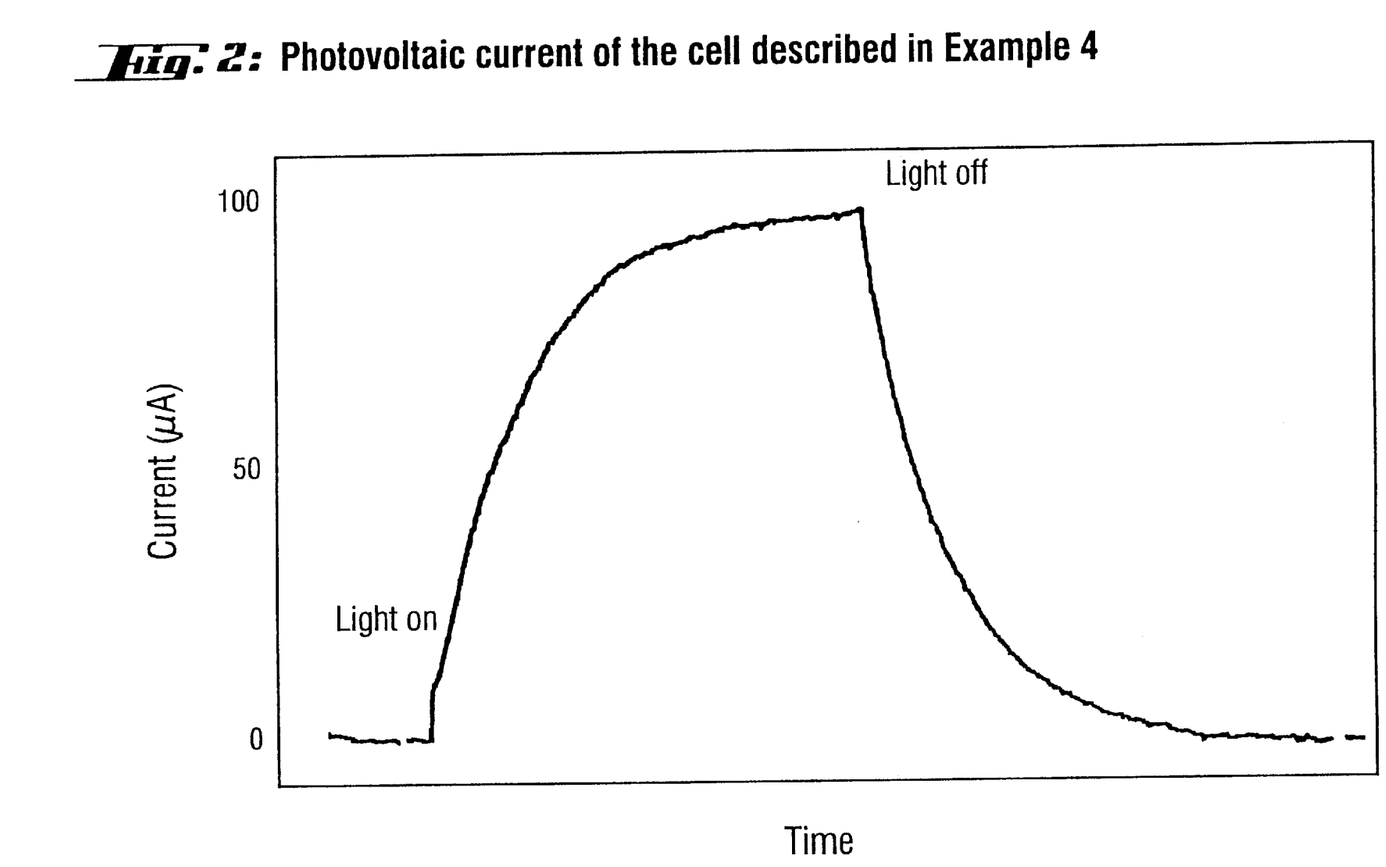
FIG. 2 shows a photovoltaic current of the cell described in Example 4.

Contacts were applied to the gold and SnO$_2$ layers and a current measuring instrument was connected while the specimen was illuminated. No external voltage was applied. During illumination of the specimen, a current was observed and this disappeared again after shutting off the light source. Comparison with a thermal treatment of the specimen showed that the current observed was a genuine photovoltaic current which arises as a result of injection of positive charge carriers (holes) into the layer of Compound 1 and transport of the holes through this layer. The intensity of the illumination was varied over a factor of ten; over this range, the photovoltaic current increased linearly with the intensity. The photovoltaic current was a multiple of the photovoltaic current of the specimen described in Example 7, which indicates that Compound 1 penetrates into the pores of the layer (see FIG. 2).

Example 9

The specimen described in Example 7 was mounted in an optical apparatus comprising a pulsed, variable frequency laser, a white light source, a monochromator and imaging and detection optics. The laser delivered pulses having a duration of about 2 ns at 30 Hz and at a wavelength of 420 nm, i.e. outside the absorption range of Compound 1, but still within the absorption range of the Nb-doped titanium dioxide layer. While the specimen was irradiated in this manner, the transient absorption of the free-radical cation of Compound 1 at 500 nm was observed. The rise in the absorption took place within the time resolution of the experiment. This indicates a very effective and rapid injection of the charge carriers into the layer of Compound 1.

Example 10

A nanoporous layer of TiO$_2$ was applied by screen printing using a suspension prepared by the sol-gel method to an SnO$_2$-coated glass support and was dried in a hot air stream at about 400° C. for about 20 minutes. The thickness of the layer is about 1.5 μm, the layer consists virtually entirely of the anatase phase and thus has no absorption above 400 nm. The coated support was dipped at a temperature of about 50° C. into a 10$^{-4}$M ethanolic solution of ruthenium tris(2,2'-bipyridyl-4,4'-dicarboxylate). After about 2 hours, the support was taken from the solution, rinsed with ethanol and dried briefly in a warm air stream. The layer system had a maximum absorbance of about 0.2 at about 500 nm. The area of the specimen was about 0.3 cm$^2$.

100 mg of Compound 2 were dissolved in 5 ml of chloroform. The solution was soaked into the pores of the layer by dipping capillary tubes into the solution and dabbing them onto the dye surface. A drop of the solution was then placed directly onto the surface and dried at room temperature. The coated support was then mounted in a vapor deposition apparatus in which a further 100 nm thick layer of Compound 2 was applied by means of thermal vapor deposition in a vacuum of about $10^{-5}$ mbar. The coated support was further coated in a vapor deposition apparatus with a 200 nm thick layer of gold as counter electrode.

The specimen thus prepared was mounted in the apparatus described in Example 7. For the measurements, the light having a wavelength of less than 430 nm was blocked out by use of appropriate optical filters. In addition, the apparatus was adjusted so that the intensity of the radiation corresponded approximately to the intensity of sunlight in central Europe (about 750 W/m$^2$).

Figure 3:
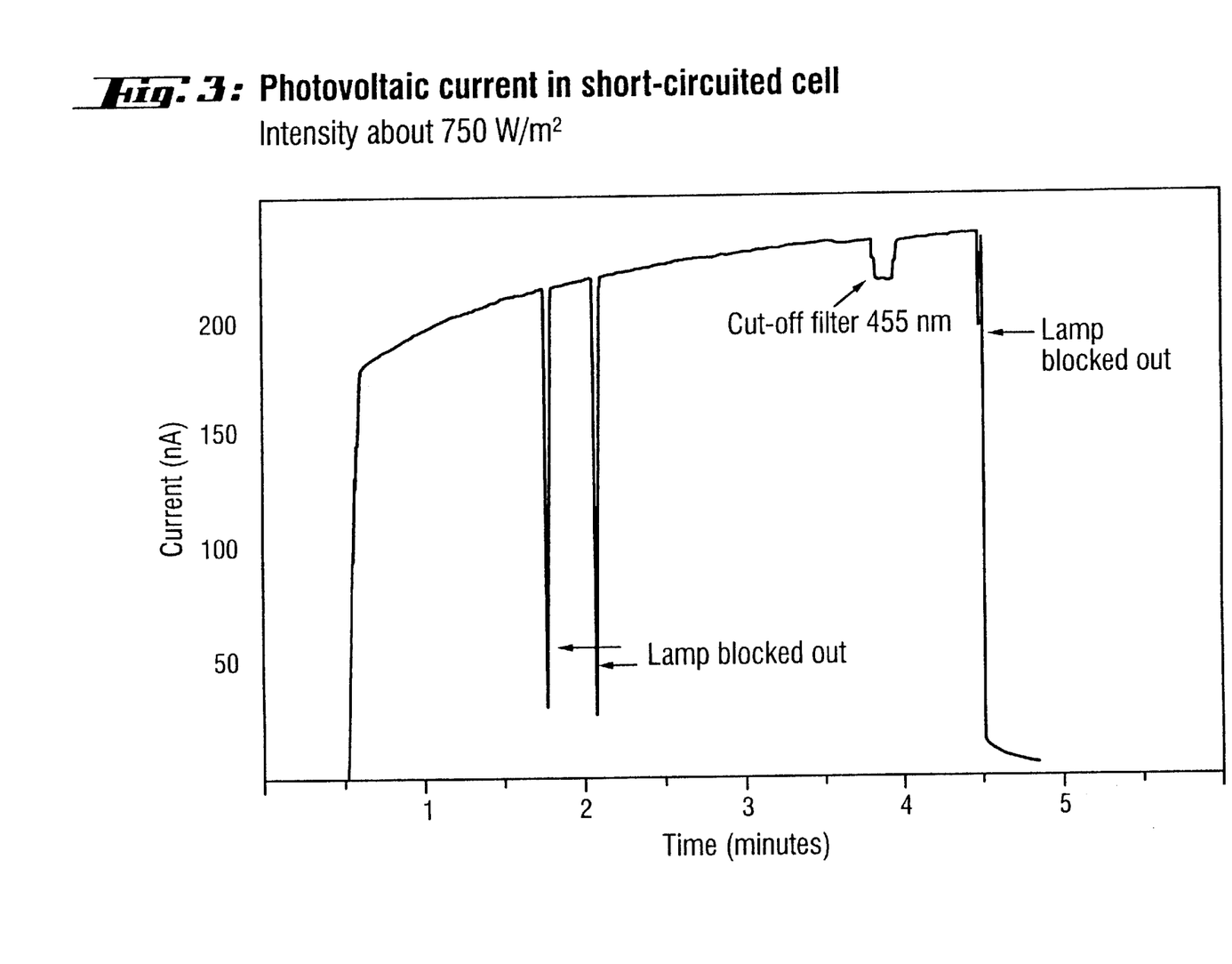
FIG. 3 shows a photovoltaic current in short-circuited cells.

Contacts were applied to the gold and SnO$_2$ layers and these were connected to a potentiostat while the specimen was illuminated. Without an external voltage, the specimen produced a current of about 200 nA, but no current without illumination. When a cut-off filter at 470 nm was installed, the decrease in the photovoltaic current corresponded approximately to the decrease in the light absorption of the dye (see FIG. 3).

Figure 4:
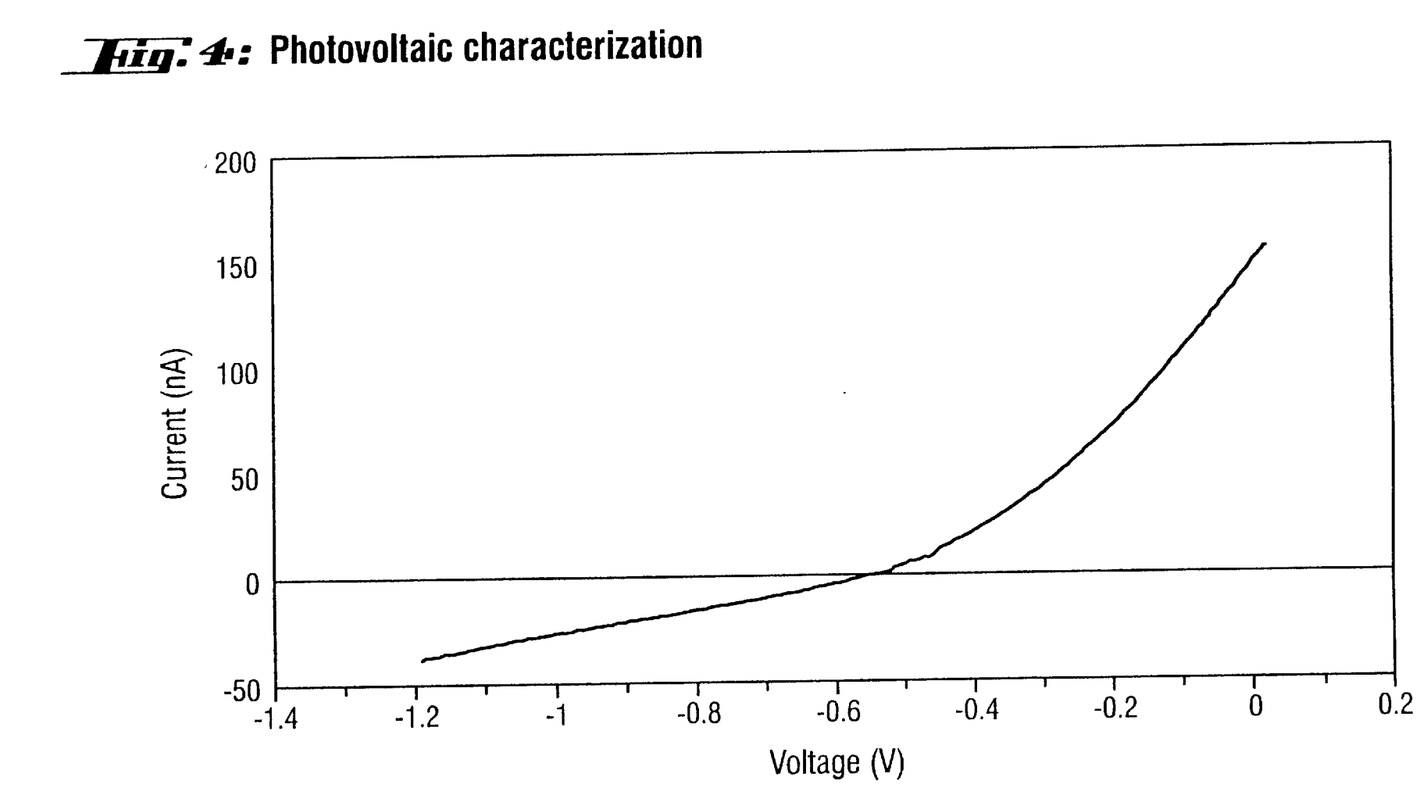
FIG. 4 shows photovoltaic characterization both with and without illumination.

The current-voltage characteristics of the sample were measured with and without illumination. Without illumination, no measurable current flowed, even when an external voltage was applied. With illumination, the characteristics of a photovoltaic cell having an open-circuit voltage of about 500–600 mV and a short-circuit current of about 800 nA/cm$^2$ were measured (see FIG. 4)

Example 11

A nanoporous layer of TiO$_2$ was applied by screen printing using a suspension prepared by the sol-gel method to an SnO$_2$-coated glass support and was dried in a hot air stream at about 400° C. for about 20 minutes. The thickness of the layer is about 1.5 μm, the layer consists virtually entirely of the anatase phase and thus has no absorption above 400 nm. The coated support was dipped at a temperature of about 50° C. into a $10^{-4}$M ethanolic solution of ruthenium tris(2,2'-bipyridyl-4,4'-dicarboxylate). After about 2 hours, the support was taken from the solution, rinsed with ethanol and dried briefly in a warm air stream. The layer system had a maximum absorbance of about 0.2 at about 500 nm. The area of the specimen was about 0.3 cm$^2$.

100 mg of Compound 2 were dissolved in 5 ml of chlorobenzene. The solution was soaked into the pores of the layer by dipping the substrate into the solution and extracting it at insertion and extraction rates of 5 cm/min. The coated support was then mounted in a vapor deposition apparatus in which a further 100 nm thick layer of Compound 2 was applied by means of thermal vapor deposition in a vacuum of about $10^{-5}$ mbar. The coated support was further coated in a vapor deposition apparatus with a 200 nm thick layer of gold as counter electrode.

The specimen thus prepared was mounted in the apparatus described in Example 7. For the measurements, the light having a wavelength of less than 430 nm was blocked out by use of appropriate optical filters. In addition, the apparatus was adjusted so that the intensity of the radiation corresponded approximately to the intensity of sunlight in central Europe (about 750 W/m$^2$).

Contacts were applied to the gold and SnO$_2$ layers and these were connected to a potentiostat while the specimen was illuminated. Without an external voltage, the specimen produced a current of about 7 μA, but no current without illumination.

The current-voltage characteristics of the sample were measured with and without illumination. Without illumination, no measurable current flowed, even when an external voltage was applied. With illumination, the characteristics of a photovoltaic cell having an open-circuit voltage of about 500 mV and a short-circuit current of about 14 μA/cm$^2$ were measured.

We claim:

1. A photovoltaic cell, comprising
   a light absorbing layer which comprises a semiconductor material with a band gap of at least 3.0 Ev, and the surface of said semiconductor having a roughness factor of >20,
   optionally a sensitizer layer,
   a charge transport layer, comprising a hole conductor material which is an amorphous solid, and
   a counter electrode.

2. The photovoltaic cell as claimed in claim 1, wherein the voltage loss across the charge transport layer is not more than 500 Mv.

3. The photovoltaic cell as claimed in claim 1, wherein the hole conductor material used is one or more spiro compounds of the formula (I)

where
   Ψ is C, Si, Ge or Sn, and
   K$^1$ and K$^2$, independently of one another, are conjugated systems.

4. A photovoltaic cell as claimed in claim 3, wherein the hole conductor material used is one or more 9,9'-spirobifluorene derivatives of the formula (II)

where Ψ is as defined in claim 3 and the benzo groups can, independently of one another, be substituted and/or fused.

5. The photovoltaic cell as claimed in claim 3, wherein the Ψ is C, Si and Ge.

6. The photovoltaic cell as claimed in claim 3, wherein the Ψ is C and Si.

7. The photovoltaic cell as claimed in claim 3, wherein the Ψ is C.

8. A photovoltaic cell as claimed in claim 1, wherein the semiconductor material is a metal oxide.

9. A photovoltaic cell as claimed in claim 1, which comprises a dye as sensitizer.

10. A process for producing a photovoltaic cell as claimed in claim 1, which comprises a) applying colloid of a semiconductor having a band gap of in a way that the resulting surface of said semiconductor has a roughness factor of >20, and a band gap of at least 3.0 Ev to a conductive solid support, b) optionally applying a dye to the semiconductor, c) applying a transport layer comprising a hole conductor material which is an amorphous solid to the dye, d) applying a counter electrode to the transport layer and e) applying an insulating layer to the counter electrode.

11. A photovoltaic cell, comprising a light absorbing layer, optionally a sensitizer layer, a charge transport layer comprising one or more spiro compounds of the formula (I) as a hole conductor material

(I)

where

Ψ is C, Si, Ge or Sn, and $K^1$ and $K^2$, independently of one another, are conjugated systems.

12. A photovoltaic cell as claimed in claim 11, wherein the hole conductor material used is one or more spirobifluorene derivatives of the formula (III),

(III)

where the symbols and indices have the following meanings:

Ψ is C, Si,

K, L, M, N are identical or different and are

R can be identical or different and as defined for K, L, M, N or be —H, a linear or branched alkyl, alkoxy or ester group having from 1 to 22, —CN, —NR$^2$R$^3$,—Ar or —O—Ar;

Ar is phenyl, biphenyl, 1-naphthyl, 2-naphthyl, 2-thienyl, 2-furanyl, 9-anthryl, where each of these groups can bear one or two radicals R;

m, n, p are 0, 1, 2 or 3;

X, Y are identical or different and are CR or nitrogen;

Z is —O—, —S—, —NR$^1$—, —CR$^1$R$^4$——CH═CH—, —CH═N—;

$R^1$, $R^4$ can be identical or different and be as defined for R;

$R^2$, $R^3$ are identical or different and are H, a linear or branched alkyl group having from 1 to 22 carbon atoms, —Ar, 3-methylphenyl.

13. The photovoltaic cell as claimed in claim 12, wherein R can be identical or different and as defined for K, L, M, N or be —H, a linear or branched alkyl, alkoxy or ester group having from 1 to 15 carbon atoms.

14. The photovoltaic cell as claimed in claim 12, wherein R can be identical or different and as defined for K, L, M, N or be —H, a linear or branched alkyl, alkoxy or ester group having from 1 to 12 carbon atoms.

* * * * *